US012629515B2

(12) United States Patent
Yoon et al.

(10) Patent No.: US 12,629,515 B2
(45) Date of Patent: May 19, 2026

(54) SYSTEM FOR PLANNING TUMOR-TREATING ELECTRIC FIELDS BASED ON TEMPERATURE CONTROL AND ABSORBED ENERGY IN BODY AND SYSTEM FOR PERFORMING ELECTRIC FIELD THERAPY INCLUDING THE SAME

(71) Applicants: KOREA UNIVERSITY RESEARCH AND BUSINESS FOUNDATION, Seoul (KR); FIELDCURE CO., LTD., Seoul (KR)

(72) Inventors: Myong Geun Yoon, Gapyeong-gun (KR); Geon Oh, Seoul (KR); Yun Hui Jo, Seoul (KR); Jong Hyun Kim, Seoul (KR)

(73) Assignees: KOREA UNIVERSITY RESEARCH AND BUSINESS FOUNDATION, Seoul (KR); FIELDCURE CO., LTD., Seoul (KR)

( * ) Notice: Subject to any disclaimer, the term of this patent is extended or adjusted under 35 U.S.C. 154(b) by 420 days.

(21) Appl. No.: 18/128,200

(22) Filed: Mar. 29, 2023

(65) Prior Publication Data

US 2023/0256243 A1    Aug. 17, 2023

Related U.S. Application Data

(63) Continuation of application No. PCT/KR2020/015278, filed on Nov. 4, 2020.

(30) Foreign Application Priority Data

Sep. 29, 2020    (KR) ........................ 10-2020-0126508

(51) Int. Cl.
*A61N 1/36*        (2006.01)
*A61B 5/00*        (2006.01)
(Continued)

(52) U.S. Cl.
CPC ........ *A61N 1/36002* (2017.08); *A61B 5/4836* (2013.01); *A61N 1/36031* (2017.08);
(Continued)

(58) Field of Classification Search
CPC ............ A61N 1/36002; A61N 1/36031; A61N 1/36034; A61N 1/08; A61N 1/36;
(Continued)

(56) References Cited

U.S. PATENT DOCUMENTS 10,607,738 B2 *  3/2020  Davidson ............... G16H 50/50
2013/0316318 A1 *  11/2013  Frank ..................... A61B 34/25
                                                                    434/262
(Continued)

FOREIGN PATENT DOCUMENTS

JP          6588158 B2      9/2019
JP          6670107 B2      3/2020
(Continued)

OTHER PUBLICATIONS

Hershkovich, H. S., et al. "Power Density Loss and Related Measures can be used to Quantify the Dose of Tumor Treating Fields (TTFields)." International Journal of Radiation Oncology, Biology, Physics 102.3 (2018): e533. (Year: 2018).*
(Continued)

*Primary Examiner* — Michael W Kahelin
*Assistant Examiner* — Attiya Sayyada Hussaini
(74) *Attorney, Agent, or Firm* — NSIP Law

(57)                ABSTRACT

Provided is a system for planning tumor-treating electric fields based on temperature control and absorbed energy in body, comprising a setting unit initially setting the number of electrodes, an electrode location, a duration and strength of voltage for each; a calculating unit calculating absorbed dose and temperature distribution in the body based on the initial settings; an evaluating unit evaluating the calculated
(Continued)

1200 absorbed dose and temperature distribution in the body to determine if they meet a preset reference; a changing unit changing at least one of the number of electrodes, the electrode location, the duration or strength of voltage for each electrode when the preset reference is not met; and a planning unit deriving an optimal electric field treatment plan by performing an optimization process including repeating the calculation, the determination and the changing steps until the dose distribution and temperature distribution in the body meet the preset reference.

20 Claims, 12 Drawing Sheets

(51) Int. Cl.
    *A61B 5/055*       (2006.01)
    *G06T 7/11*        (2017.01)

(52) U.S. Cl.
    CPC .......... *A61N 1/36034* (2017.08); *A61B 5/055* (2013.01); *G06T 7/11* (2017.01)

(58) Field of Classification Search
    CPC ........ A61N 1/40; A61N 1/3603; A61B 5/055; A61B 5/4836; A61B 5/0036; A61B 5/7264; A61B 6/03; A61B 5/0537; A61B 6/032; A61B 6/5217; G06T 7/11; G16H 20/30
    See application file for complete search history.

(56)          References Cited

U.S. PATENT DOCUMENTS

| | | | |
|---|---|---|---|
| 2014/0330268 A1* | 11/2014 | Palti ........................ | A61P 35/00 |
| | | | 606/34 |
| 2017/0120041 A1 | 5/2017 | Wenger et al. | |

FOREIGN PATENT DOCUMENTS

| | | | |
|---|---|---|---|
| JP | 2020-091293 A | 6/2020 | |
| JP | 6767030 B2 | 10/2020 | |
| KR | 10-1721798 B1 | 3/2017 | |
| KR | 10-2020-0004228 A | 1/2020 | |

OTHER PUBLICATIONS

Pennes "Analysis of Tissue and Arterial Blood Temperatures in the Resting Human Forearm" *Journal of Applied Physics* vol. 1 Number 2. Aug. 1948 (pp. 93-122).

Kirson et al. "Disruption of Cancer Cell Replication by Alternating Electric Fields" *Cancer research* vol. 64 Number 9. May 1, 2004 (pp. 1-8).

Kirson et al. "Alternating electric fields arrest cell proliferation in animal tumor models and human brain tumors" *Proceedings of the National Academy of Sciences* vol. 104 No. 24. Apr. 5, 2007 (pp. 1-6).

Kirson et al. "Alternating electric fields (TTFields) inhibit metastatic spread of solid tumors to the lungs" *Clinical & experimental metastasis* vol. 26. Apr. 23, 2009 (pp. 1-8).

Pless et al. "Tumor treating fields: concept, evidence and future" *Expert opinion on investigational drugs* vol. 20 No. 8. 2011 (pp. 1099-1106).

Davies et al. "Tumor treating fields: a new frontier in cancer therapy" *Annals of the New York Academy of Sciences* vol. 1291 No. 1. 2012 (pp. 86-95).

Stupp et al. "Effect of Tumor-Treating Fields Plus Maintenance Temozolomide vs Maintenance Temozolomide Alone on Survival in Patients With Glioblastoma A Randomized Clinical Trial" *Jama* vol. 318 No. 23. 2017 (pp. 2306-2316).

Fabian et al. "Treatment of Glioblastoma (GBM) with the Addition of Tumor-Treating Fields (TTF): A Review" *Cancers* vol. 11 No. 2. Feb. 2, 2019 (pp. 1-12).

Jo et al. "Effectiveness of a Fractionated Therapy Scheme in Tumor Treating Fields Therapy" *Technology in cancer research & treatment* vol. 18. Mar. 21, 2019 (pp. 1-10).

International Search Report for PCT Application PCT/KR2020/015278 Jun. 23, 2021.

Novocure GmbH "PatientForward" *Novocure Corporate Presentation* Feb. 2023 (pp. 1-40).

\* cited by examiner

FIG. 1
(a)
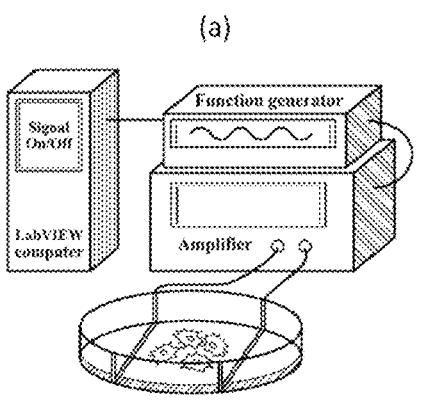
(b)
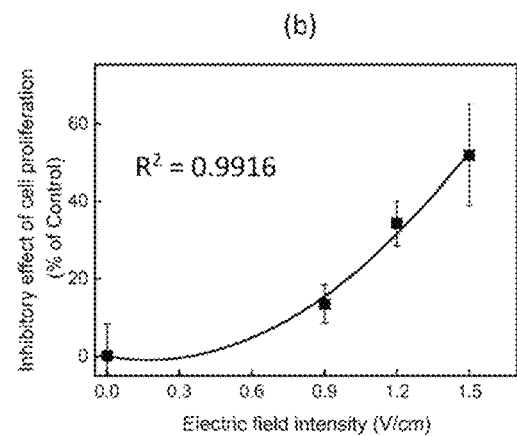

FIG. 2
(a)
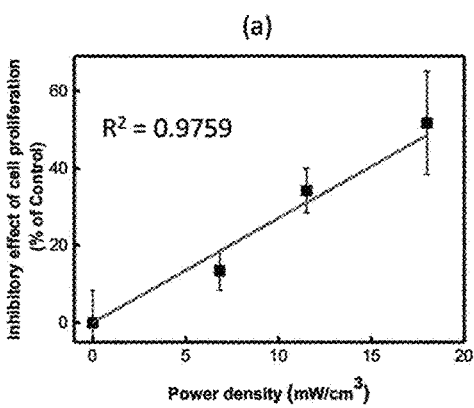
(b)
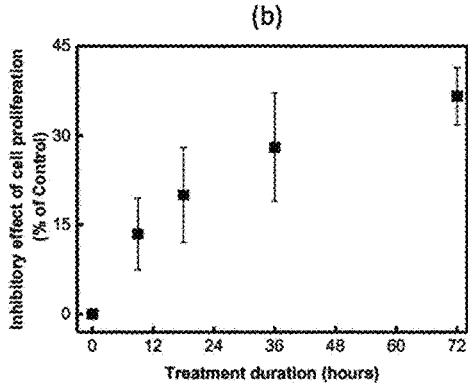

FIG. 3
(a)
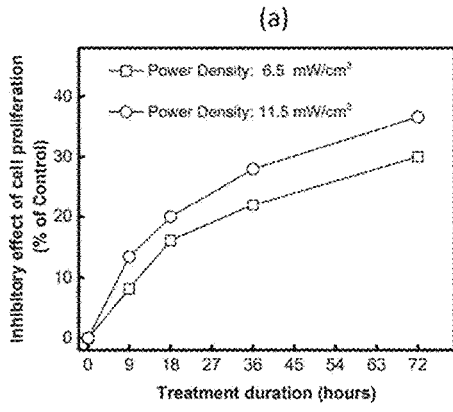
(b)
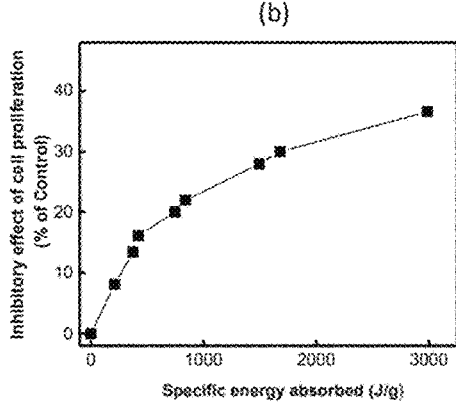

FIG. 7

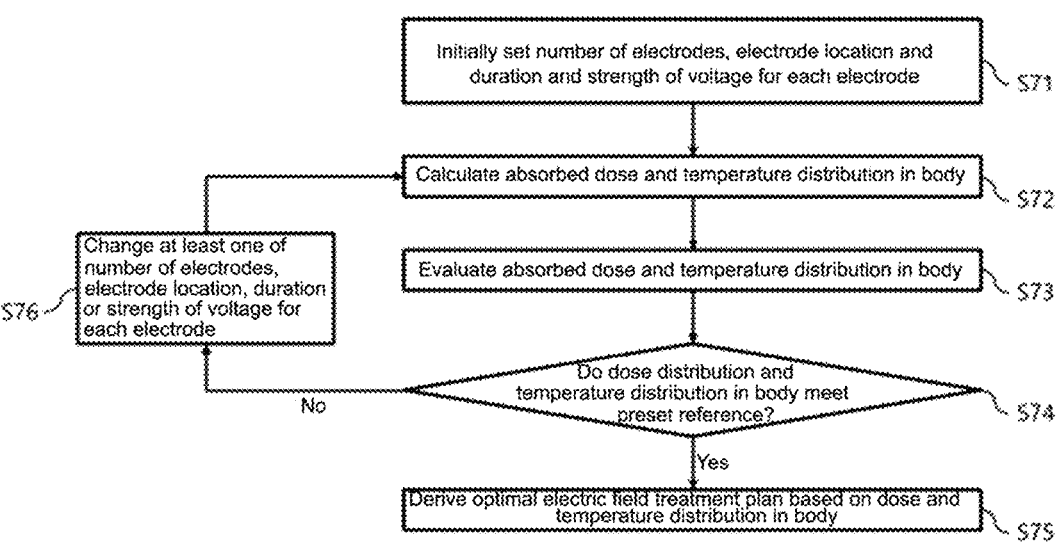

Initially set number of electrodes, electrode location and duration and strength of voltage for each electrode    S71

Calculate absorbed dose and temperature distribution in body    S72

Evaluate absorbed dose and temperature distribution in body    S73

Change at least one of number of electrodes, electrode location, duration or strength of voltage for each electrode    S76

Do dose distribution and temperature distribution in body meet preset reference?    S74

No

Yes

Derive optimal electric field treatment plan based on dose and temperature distribution in body    S75

FIG. 8
(a)  Treatment time = 1 hour/day for 3 days
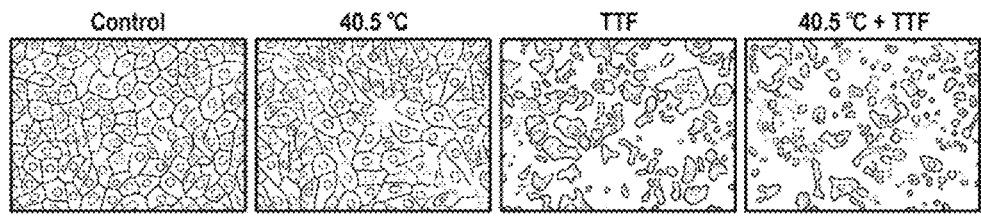
(b)
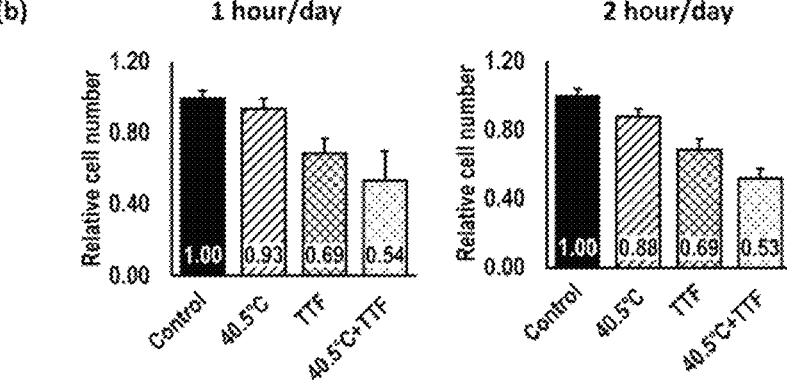

FIG. 9
(a)
Hyperthermia + TTF
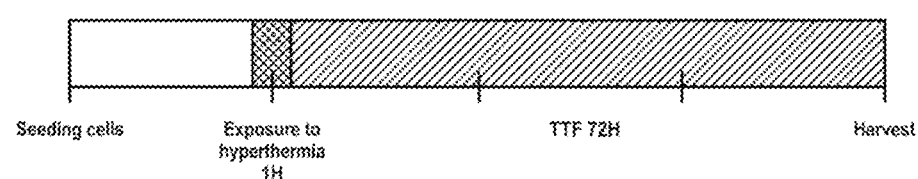
Seeding cells     Exposure to     TTF 72H     Harvest
                  hyperthermia
                  1H
(b)
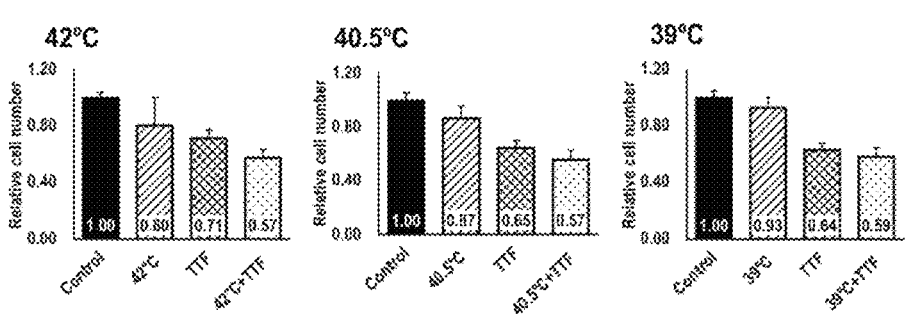

1200

SYSTEM FOR PLANNING TUMOR-TREATING ELECTRIC FIELDS BASED ON TEMPERATURE CONTROL AND ABSORBED ENERGY IN BODY AND SYSTEM FOR PERFORMING ELECTRIC FIELD THERAPY INCLUDING THE SAME

CROSS REFERENCE TO RELATED APPLICATIONS

This application is a PCT Continuation By-Pass Application of International Application No. PCT/KR2020015278, filed on Nov. 4, 2020, which claims the benefit under 35 USC 119 (a) and 365(b) of Korean Patent Application No. 10-2020-0126508, filed on Sep. 29, 2020, in the Korean Intellectual Property Office, the entire disclosures of which are incorporated herein by reference for all purposes.

TECHNICAL FIELD

The present disclosure relates to a system for planning tumor-treating electric fields based on temperature control and absorbed energy in body and a system for performing electric field therapy comprising the same, and more particularly, to a system for planning tumor-treating electric fields based on temperature control and absorbed energy in body to maximize the treatment effects of electric fields transmitted to tumors while maintaining a temperature change for heating therapy on cancer tissue preventing side effects such as burns in normal tissues by controlling a temperature rise in each tissue in human body occurring by the electric fields applied for tumor treatment, and a system for electric field therapy comprising the same.

BACKGROUND ART

In the early 2000s, Yoram Palti, an Israel professor of physiology, first found that alternating electric fields applied to dividing cancer cells disrupt cell mitosis or induce cell death, and in 2004, published the research results about cancer treatment effects of electric fields in the Journal of Cancer Research first in the world. Subsequently, many research papers about electric field cancer treatment have been published, and in the research area of cancer treatment, much attention is paid to electric field therapy due to three advantages.

The first advantage of electric field therapy is that since it is known that electric fields only have great influence on dividing cells, it is expected that electric field therapy will greatly affect cancer cells that divide faster than normal cells and have much fewer side effects than the existing therapy. Actually, according to the paper published in 2013, in the comparison of side effects between anti-cancer therapy and electric field therapy, in 7 items among the total of 9 items, side effects of electric field therapy are much lower, and in 2 items, anti-cancer therapy and electric field therapy show almost equal level of side effects.

Secondly, cancer therapy using electric fields is in the early stage yet, but shows better results than the existing therapy in terms of treatment efficacy. For example, when patients of malignant glioblastoma multiforme (GBM), one of incurable cancers, only receive anti-cancer therapy, Progression Free Survival (PFS), Overall Survival (OS) and 2-year survival rate are 4.0 months, 16.0 months and 31%, respectively, but when electric field therapy is added, PFS, OS and 2-year survival rate are 6.7 months, 20.9 months and 43%, respectively, showing the results that are about 1.7, 1.3 and 1.4 times higher than the existing therapy.

Finally, the third advantage is that when electric fields are applied over wide areas including treatment sites, it is expected that there will be treatment effects on tumors that are so small as to be invisible in medical images such as computed tomography (CT) images. When electric fields are applied to tumors, in addition to the tumors, nonnegligible electric fields are transmitted to areas near the tumors, so it is possible to inhibit the division of cancer cells by the influence of the electric fields on tumors that exist near the tumors but are so small as to be invisible to the eyes, thereby remarkably reducing the probability of cancer metastasis.

Currently, electric field cancer treatment was approved by U.S. Food and Drug Administration (FDA) for recurrent glioblastoma multiforme in 2011 and original glioblastoma multiforme in 2015 and obtained the CE mark in Europe and is being conducted through about 1000 hospitals in USA, Germany, Switzerland and so on, and treatment for recurrent glioblastoma multiforme patients was approved in Japan. Additionally, the number of patients who have received treatment is dramatically increasing every year, and there is an increase of 20 times or more from 152 patients in 2014 to 8813 patients in 2018.

However, there are some challenges to overcome faced by the current electric field cancer treatment in order to maximize the treatment effect.

According to the research results to date, there is a difference in cell proliferation inhibitory effect of electric fields for each cancer type depending on the intensity and duration of electric fields applied to human body, and with the increasing intensity and duration of electric fields, there are larger effects of killing cancer cells and inhibiting the division of cancer cells. Accordingly, to achieve the desired treatment effect, it is essential to increase the intensity and duration of electric fields.

The current commercially available systems for electric field cancer treatment have been developed to perform treatment using low intensity electric fields of about 1 to 3 V/cm, and to obtain the maximum treatment effect using low intensity electric fields, patients need to receive treatment almost all day long (18-24 hours/day) except when the patients are sleeping, causing inconvenience to the patients.

Additionally, increasing the daily treatment duration has already reached its limit, and in this case, it is indispensable to apply electric fields of sufficient magnitude to obtain the treatment effect. Increasing the intensity of electric fields transmitted to the body by simply increasing the magnitude of applied voltage is physically possible. However, the increased electric fields transmit heat to the skin and each tissue in the body, causing serious side effects such as burns to each tissue or organs at risk in the human body including the skin. By this reason, the magnitude of thermal energy transmitted to each tissue in the human body and the temperature rise in each tissue may be important considerations in electric field therapy. The current electric field cancer treatment monitors the temperature of the skin by controlling the electric currents flowing in the skin by electrodes, but there is no system that performs treatment while controlling the temperature change in the tissues in the human body regarded as the more important consideration.

Accordingly, it is necessary to not only maximize the intensity of electric fields transmitted to tumors but also control the temperature rise in normal tissues in the body occurring by the electric fields below a predetermined level in order to minimize side effects caused by the heat in electric field therapy and maximize the tumor treatment effect.

DISCLOSURE

Technical Problem

Accordingly, the corresponding technical field needs an approach to control thermal energy transmitted into human body in electric field therapy to prevent the temperature rise in normal tissues in the body above the threshold, thereby preventing side effects such as burns as well as maximizing the intensity of electric fields transmitted to tumors, thereby maximizing the cancer treatment effect of the electric fields. Also, the heating therapy killing cancer cell without harming normal cell can be expected when the temperature can be controlled within the preset temperature range which affects only cancer cells without affecting normal cells substantially.

The objective of the present disclosure is not limited to the above-mentioned objective, and these and other objectives will be clearly understood by those skilled in the art from the following description.

Technical Solution

To solve the above-described problem, an embodiment of the present disclosure provides a system for planning tumor-treating electric fields based on temperature control and absorbed energy in body, comprising: a setting unit initially setting the number of electrodes, an electrode location, a duration and strength of voltage for each; a calculating unit calculating absorbed dose and temperature distribution in the body based on the initial settings; an evaluating unit evaluating the calculated absorbed dose and temperature distribution in the body to determine if they meet a preset reference; a changing unit changing at least one of the number of electrodes, the electrode location, the duration or strength of voltage for each electrode when the preset reference is not met; and an planning unit deriving an optimal electric field treatment plan by performing an optimization process including repeating the calculation step, the determination step and the changing step until the dose distribution and temperature distribution in the body meet the preset reference.

The setting unit initially sets the number of electrodes, an electrode location, a duration and strength of voltage for each based on pre-input patient information.

The system may further comprises a segmenting unit segmenting a region of interest including a tumor and an organ in a patient's medical image; a dose-determining unit determining a prescribed dose based on absorbed energy in consideration of input tumor type and tumor condition information; and a prescription-determining unit determining prescription information including a total treatment number, a total treatment duration, a daily treatment duration and a treatment frequency for electric field therapy; wherein the setting unit initially the number of electrodes, an electrode location, a duration and strength of voltage for each electrode in consideration of the tumor and organ.

In one embodiment of the present invention, the evaluating unit utilizes the property information of human body when evaluating the calculated absorbed dose and temperature.

In one embodiment of the present invention, The property information includes electrical conductivity, thermal conductivity, specific heat and mass density of each tissue in the human body.

In one embodiment of the present invention, the electrical conductivity is set based on magnetic resonance imaging (MRI) or a pre-built electrical conductivity database (DB) for each tissue in the human body.

In one embodiment of the present invention, the mass density is set based on computed tomography (CT) or a pre-built mass density DB for each tissue in the human body.

In one embodiment of the present invention. the thermal conductivity and specific heat are set based on a pre-built thermal conductivity and specific heat DB for each tissue in the human body.

Additionally, another embodiment of the present disclosure provides a system for performing electric field therapy, comprising the system for planning tumor-treating electric fields based on temperature control and absorbed energy in the body according to the system as mentioned above; an electric field therapy device performing electric field therapy in compliance with the plan set by the system for planning tumor-treating electric fields based on temperature control and absorbed energy in body; a heating device; wherein the heating device performs heat therapy by maintaining the temperature of a region of interest including a tumor in a preset temperature range for a preset time, and the electric field therapy device performs electric field therapy according to the plan set by the treatment planning system at the same time with or after the heat therapy.

In one embodiment of the present invention, the preset temperature range affects only cancer cells without affecting normal cells substantially.

The effect of the present disclosure is not limited to the above-mentioned effect, and these and other effects will be clearly understood by those skilled in the art from the following description.

DESCRIPTION OF DRAWINGS

FIG. 1 is a diagram showing the cell proliferation inhibitory effect as a function of intensity of applied electric fields.

FIG. 2 is a diagram showing the cell proliferation inhibitory effect as a function of power loss density and duration of applied electric fields.

FIG. 3 is a diagram showing the cell proliferation inhibitory effect at different power loss densities and different durations of applied electric fields.

FIG. 7 is a flowchart of a method for planning tumor-treating electric fields based on temperature control and absorbed energy in body according to an embodiment of the present disclosure.

FIG. 8 is a diagram showing the enhanced cell proliferation inhibitory effect when electric fields of 150 kHz are applied at the same time with maintaining the temperature of tumor cells in the 40.5° C. range for a predetermined time.

FIG. 9 is a diagram showing the enhanced cell proliferation inhibitory effect when electric fields of 150 kHz are applied after maintaining the temperature of tumor cells in the range of 39° C. to 42° C. for a predetermined time.

BEST MODE

Figure 4:
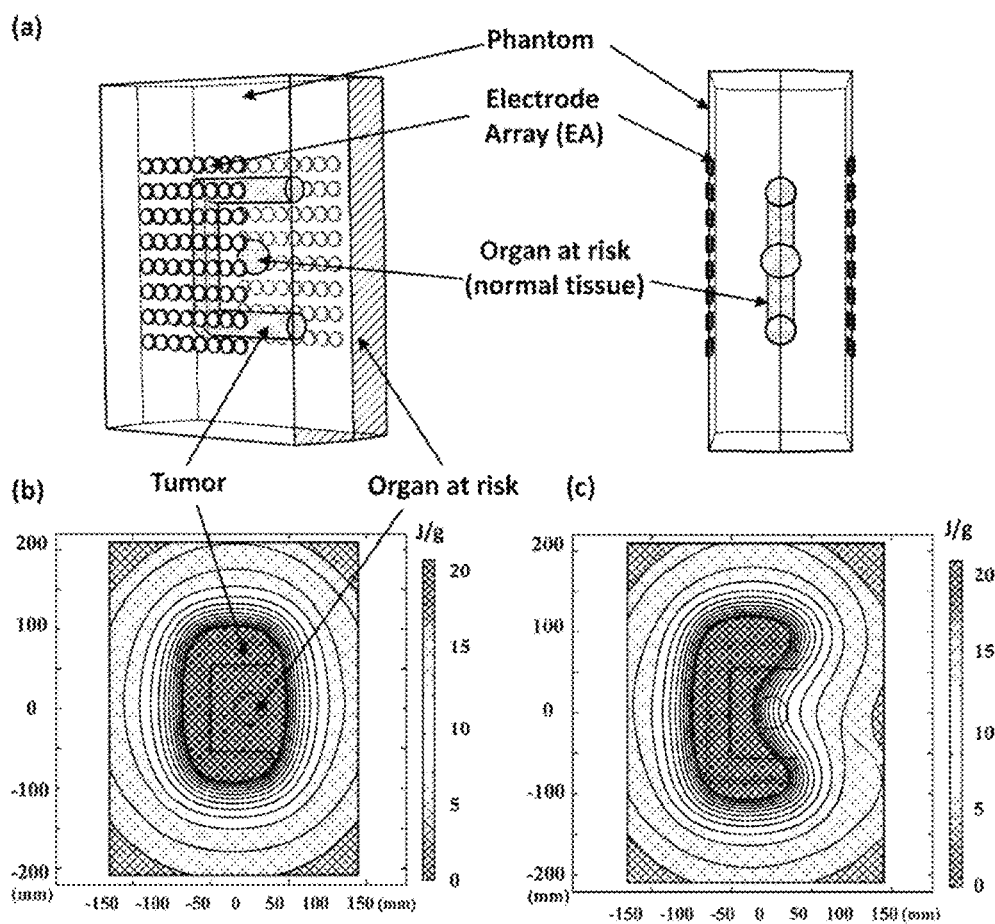
FIG. 4 is a diagram showing the result of dose optimization performed using dose unit based on absorbed energy in electric field therapy under the assumption of an imaginary tumor and an organ at risk (OAR) including normal cells in a human body model phantom.

Hereinafter, an exemplary embodiment will be described in sufficient detail with reference to the accompanying drawings for those skilled in the art to easily practice the present disclosure. However, in describing an exemplary embodiment of the present disclosure in detail, when it is determined that a certain detailed description of relevant known functions or elements may unnecessarily obscure the subject matter of the present disclosure, the detailed description is omitted. Additionally, identical reference signs are used for the elements having similar functions and operations throughout the drawings.

In addition, throughout the specification, when an element is referred to as being 'connected to' another element, it can be directly connected to the other element or intervening elements may be present. Additionally, unless the context clearly indicates otherwise, the term 'comprises' when used in this specification, specifies the presence of stated elements, but does not preclude the presence or addition of one or more other elements.

The present invention provides a system for planning tumor-treating electric fields based on temperature control and absorbed energy in body, comprising: a setting unit initially setting the number of electrodes, an electrode location, a duration and strength of voltage for each; a calculating unit calculating absorbed dose and temperature distribution in the body based on the initial settings; an evaluating unit evaluating the calculated absorbed dose and temperature distribution in the body to determine if they meet a preset reference; a changing unit changing at least one of the number of electrodes, the electrode location, the duration or strength of voltage for each electrode when the preset reference is not met; and an planning unit deriving an optimal electric field treatment plan by performing an optimization process including repeating the calculation step, the determination step and the changing step until the dose distribution and temperature distribution in the body meet the preset reference.

The purpose and function of each unit is to be explained in more detail below.

In FIGS. 1 to 3, the inhibitory effect of cell proliferation in malignant glioma cell line (U373) (an experimental group) to which electric fields having the intensity of ~1 V/cm and the frequency of 150 kHz are applied is indicated in percentage relative to a control group by comparing the cell viability between the experimental group and the control group through cell counting after applying the electric fields to the cell line. This result represents an average value of three experiments, and the cell proliferation inhibitory effect in percentage relative to the control group is calculated by the following Equation 1.

$$\begin{aligned}\text{Cell proliferation inhibitory effect } (\%) = (1 - \text{Number} \\ \text{of cells of experimental group/Number of cells} \\ \text{of control group}) \times 100 \qquad \text{[Equation 1]}\end{aligned}$$

For example, when the number of cells that survive in the experimental group to which the electric fields are applied is 70% relative to the control group, the cell proliferation inhibitory effect of the experimental group is 30% relative to the control group.

FIG. 1 is a diagram showing the cell proliferation inhibitory effect as a function of intensity of applied electric fields, (a) shows the experimental setup for verifying the cell proliferation inhibitory effect of 150 kHz alternating electric fields, and (b) is a graph showing the cell proliferation inhibitory effect as a function of electric field intensity.

Referring to (b) of FIG. 1, it can be seen that when electric fields are applied, the cell proliferation inhibitory effect has a proportional relationship with the electric field intensity. However, it can be seen that the cell proliferation inhibitory effect and the electric field intensity are closer to a non-linear relationship than simply a linear relationship. The curve shown in (b) shows the result of fitting a second order curve to data, and the coefficient of determination $R^2 = 0.9916$.

FIG. 2 is a diagram showing the cell proliferation inhibitory effect as a function of power loss density and duration of applied electric fields, (a) is a graph showing a relationship between the power loss density (power density) and the cell proliferation inhibitory effect when 150 kHz alternating electric fields are applied, and (b) is a graph showing a relationship between the duration of applied electric fields (treatment duration) and the cell proliferation inhibitory effect when the power loss density is fixed to 11.5 mW/cm³.

Referring to (a) of FIG. 2, it can be seen that when electric fields are applied, the cell proliferation inhibitory effect has a proportional relationship with the power loss density (power density). Here, the power loss density is defined as $\frac{1}{2} \sigma E^2$ ($\sigma$: electrical conductivity, E: electric field intensity), and the curve shown in (a) is the result of fitting a first order curve to data.

When comprehensively considering (b) of FIG. 1 and (a) of FIG. 2, it can be seen that when electric fields are applied, the cell proliferation inhibitory effect is directly proportional to the square of the electric field intensity rather than the electric field intensity, and thus is proportional to the power loss density more linearly ($R^2 = 0.9759$).

Additionally, referring to (b) of FIG. 2, it can be seen that when electric fields are applied, the cell proliferation inhibitory effect is proportional to the duration of the applied electric fields.

FIG. 3 is a diagram showing the cell proliferation inhibitory effect at different power loss densities and different durations of applied electric fields, (a) is a graph showing the cell proliferation inhibitory effect as a function of duration of applied electric fields when the power loss density is 6.5 mW/cm³ and 11.5 mW/cm³, and (b) is a graph showing the cell proliferation inhibitory effect as a function of absorbed energy (specific energy absorbed) per unit mass.

Referring to (a) of FIG. 3, it can be seen that when the duration of applied electric fields is equal, the higher cell proliferation inhibitory effect can be obtained at the higher power loss density.

(b) of FIG. 3 shows a relationship between the cell proliferation inhibitory effect and the specific absorbed energy, and here, the specific absorbed energy (absorbed energy per unit mass) may be calculated according to the following Equation 2.

$$\text{Specific absorbed energy} = (\text{power loss density} \times \text{duration of applied electric fields}) \div (\text{mass density}) \quad [\text{Equation 2}]$$

Referring to (b) of FIG. 3, it can be seen that when electric fields are applied, the cell proliferation inhibitory effect is proportional to specific absorbed energy. The specific absorbed energy transmitted to the cell is the concept including both the power loss density and the durations of applied electric fields which is proportional to the cell proliferation inhibitory effect and may be a more practical and reasonable reference for quantitating the cell proliferation inhibitory effect than the power loss density that does not consider the duration of applied electric fields.

FIG. 4 is a diagram showing the result of dose planning performed using dose unit based on absorbed energy in the electric field therapy under the assumption of an imaginary tumor and an organ at risk (OAR) including normal cells in the human body model phantom, (a) shows the human body model phantom including the tumor and the organ at risk, (b) shows the dose distribution before the dose optimization, and (c) shows the dose distribution after the dose optimization.

Specifically, as shown in (a) of FIG. 4, the imaginary ⊏-shaped tumor and the spherical organ at risk including normal cells in the human body model phantom are set, and 200 kHz alternating electric fields are applied.

(b) and (c) of FIG. 4 show the dose distribution of the tumor and the organ at risk before and after the dose optimization process in the body, respectively, and before the optimization process, the average specific absorbed energy applied to the tumor and the organ at risk is equally ~20 J/g, while after the optimization process, the specific absorbed energy applied to the tumor and the organ at risk is 20 J/g and 10-15 J/g, respectively, and thus it can be seen that it is possible to minimize the specific absorbed energy applied to the organ at risk while maintaining the specific absorbed energy applied to the tumor through the optimization process at a predetermined level.

Figure 5:
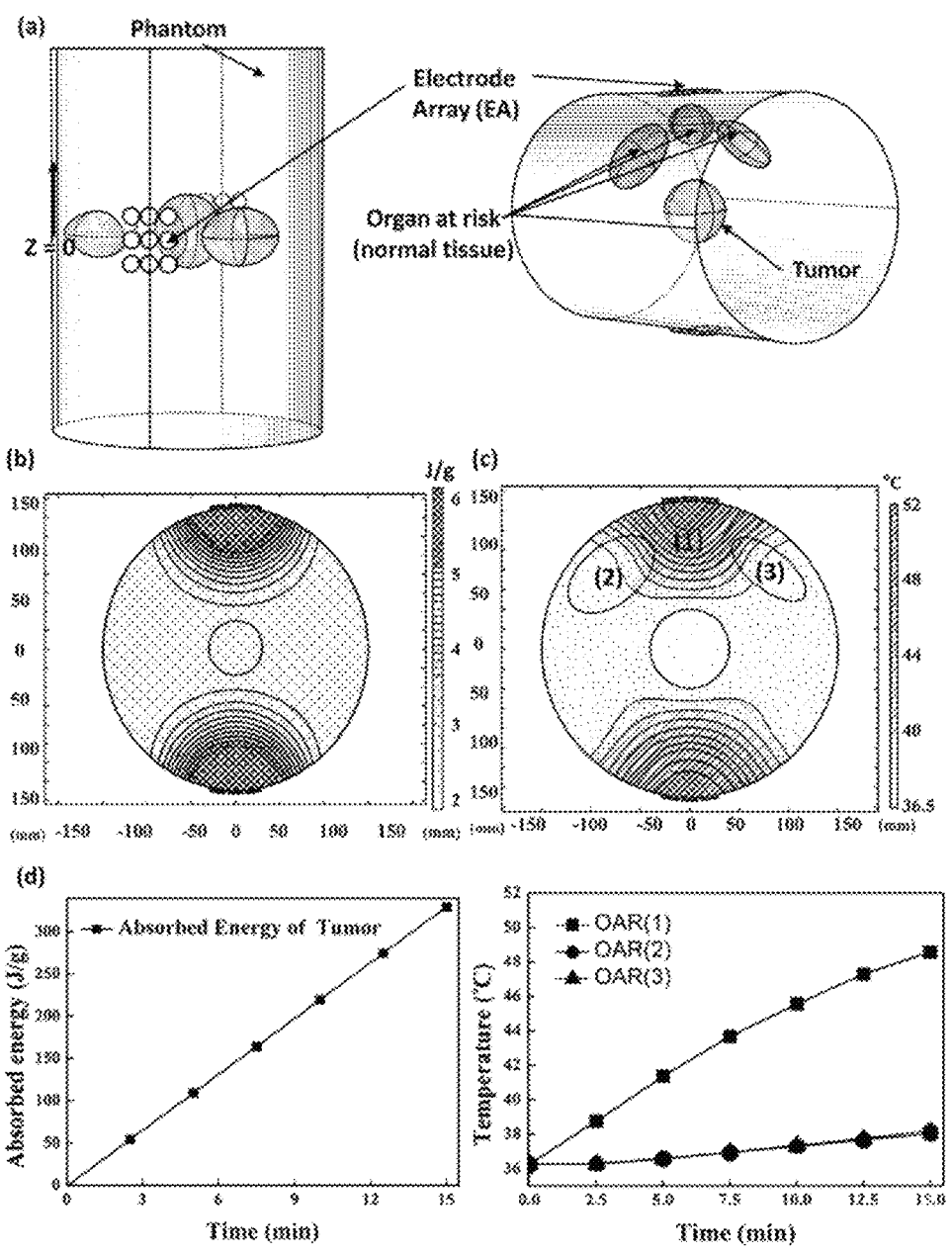
FIG. 5 is a diagram showing a specific absorbed energy distribution and a temperature distribution in a human body model phantom and a specific absorbed energy distribution of a tumor and an average temperature change for each organ at risk as a function of duration of applied electric fields when electric fields are applied using a pair of Electrode Arrays (EA) under the assumption of the imaginary tumor and three organs at risk (OARs) in the human body model phantom.

FIG. 5 shows specific absorbed energy distribution and temperature distribution in a human body model phantom and specific absorbed energy distribution of a tumor and average temperature change for each organ at risk as a function of duration of applied electric fields when electric fields are applied using a pair of electrode arrays (EA) under the assumption of the imaginary tumor and three organs at risk (OARs) in the human body model phantom, (a) shows the coronal plane and side of the human body model phantom, (b) shows the specific absorbed energy (J/g) distribution in the XY plane when Z=0, (c) shows the temperature distribution in the XY plane when Z=0 after the electric field therapy is continuously performed for 15 minutes, and (d) shows the specific absorbed energy (J/g) (left graph) transmitted to the tumor and the average temperature change (right graph) in the organs at risk 1, 2, 3 with the time passing from 0 minute to 15 minutes.

Referring to the left graph in (b) and (d) of FIG. 5, it can be seen that the total specific absorbed energy transmitted to the tumor is proportional to time, and it can be seen that when treatment is performed for 15 minutes by delivering specific absorbed energy of about 55 J/g every 2 minutes 30 seconds, the total specific absorbed energy transmitted to the tumor has a value of 330 J/g.

Additionally, referring to the right graph in (c) and (d) of FIG. 5, it can be seen that when the electric field therapy is performed for 15 minutes using a pair of electrode arrays (EA), there is a rise in temperature of the area at which the electrodes are attached as opposed to the temperature of the area at which the electrodes are not attached, and thus the average temperature of OAR(1) rises to about 49° C.

Based on this, in case that the electric field therapy is performed for a predetermined time or more using only one pair of electrode arrays when actually treating patients, normal tissues and organs at risk in the patient's body may be exposed to side effects such as burns and loss of organ function due to the temperature rise, and this suggests the need for a new type electric field therapy for preventing the side effects through the patient's body temperature control.

Figure 6:
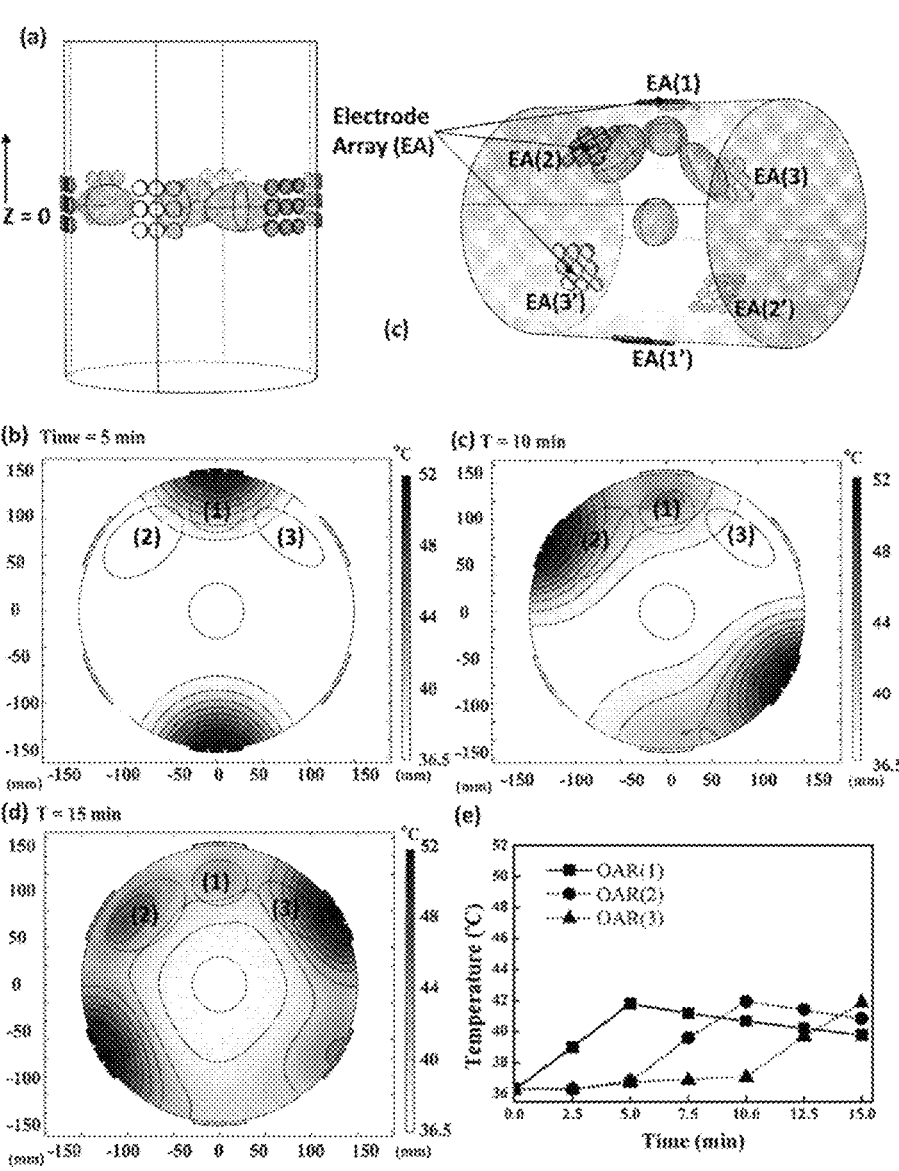
FIG. 6 is a diagram showing a temperature distribution for each organ at risk in the same human body model phantom as FIG. 5 as a function of duration of applied electric fields and an average temperature change over time when electric fields are applied to the human body model phantom for each pair of electrode arrays in a sequential order using three pairs of electrode arrays (EA).

FIG. 6 shows the temperature distribution for each organ at risk as a function of duration of applied electric fields in the human body model phantom and the average temperature change over time when electric fields are applied every pair of electrode arrays in a sequential order using three pairs of electrode arrays (EA) in the same human body model phantom as FIG. 5, (a) shows the coronal plane and side of the human body model phantom, (b) shows the temperature distribution in the XY plane when Z=0 at the point in time of 5 minutes after voltage is only applied to the electrode array EA(1, 1') from 0 minute to 5 minutes, (c) shows the temperature distribution in the same plane as (b) at the point in time of 10 minutes after voltage is only applied to the array electrode EA(2, 2') from 5 minutes to 10 minutes, (d) shows the temperature distribution in the same plane as (b) at the point in time of 15 minutes after voltage is only applied to the electrode array EA(3, 3') from 10 minutes to 15 minutes, and (e) shows the average temperature change in the organs at risk 1, 2, 3 with the time passing from 0 minute to 15 minutes.

According to the simulation calculation results, it can be seen that the total specific absorbed energy transmitted to the tumor is proportional to time in the same way as FIG. 5, and when treatment is performed for 15 minutes by delivering the specific absorbed energy of about 55 J/g every 2 minutes 30 seconds, the total specific absorbed energy transmitted to the tumor has a value of 330 J/g.

Additionally, referring to (d) of FIG. 5 and (e) of FIG. 6, when comparing the application of voltage to only one pair of electrode arrays for 15 minutes with the application of voltage to three pairs of electrode arrays for the total of 15 minutes, each for 5 minutes in a sequential order, the total specific absorbed energy transmitted to the tumor has almost similar value, and through this, it can be seen that two methods have no big difference in specific absorbed energy transmitted to the tumor.

In contrast, it can be seen that when voltage is applied to only one pair of electrode arrays for 15 minutes, the average temperature of OAR(1) rises to about 49° C., but when voltage is applied to the three pairs of electrode arrays in a sequential order, the average temperature of the three OARs does not exceed 42° C. Additionally, referring to the graph in (e) of FIG. 6, the average temperature of OAR(1) having the temperature rise for the previous 5 minutes gradually decreases while electric fields are applied to the electrode array EA(2, 2') pair, and the average temperature of OAR(1) and OAR(2) gradually decreases while electric fields are applied to the electrode array EA(3, 3') pair.

When comprehensively analyzing the results of FIGS. 5 and 6 under the assumption that the temperature limit of the organs at risk (OARs) is 42° C., it can be seen that it is possible to solve the side effect problem caused by the temperature rise in the organs at risk above the preset temperature limit while applying sufficient electric fields to the tumor by adjusting the duration of voltage applied to the pairs of electrode arrays and each electrode array.

FIG. 7 is a flowchart of a method for planning tumor-treating electric fields based on temperature control and absorbed energy in body according to an embodiment of the present disclosure. It is understood that all steps below is to be implemented by the system as mentioned above.

Referring to FIG. 7, first, the number of electrodes, the electrode location and the duration and strength of voltage for each electrode may be initially set based on pre-input patient information (S71), and the absorbed dose and temperature distribution in the body may be calculated based on the initial settings (S72).

Subsequently, the calculated absorbed dose and temperature distribution in the body may be evaluated (S73) to determine if the dose distribution and temperature distribution in the body meet the preset reference (S74).

When the preset reference is not met, the optimization process may be performed by changing at least one of the number of electrodes, the electrode location, the duration or strength of voltage for each electrode (S76), and repeatedly performing the steps S72 to S74 until the dose distribution and temperature distribution in the body meet the preset reference.

The optimal electric field treatment plan may be derived based on the dose and temperature distribution in the body by performing the optimization process (S75), thereby maximizing the electric field treatment effect by applying the maximum electric fields to the tumor without side effects caused by the temperature rise in normal tissues.

FIG. 8 is a diagram showing the enhanced cell proliferation inhibitory effect by applying electric fields of 150 kHz at the same time with maintaining the temperature of the tumor cell in the 40.5° C. range for a predetermined time.

Specifically, FIG. 8 shows the cell proliferation inhibitory effect by comparing the cell viability through cell counting between the control group and a group (TTF) in which only electric fields having the intensity of ~1 V/cm and the frequency of 150 kHz are applied to malignant glioma cell line (U373), a group (40.5° C.) in which only heat is applied to maintain the temperature of the tumor cell at 40.5° C., and a group (40.5° C.+TTF) in which heat and electric fields are applied together, and (a) shows a microscopic image of the cell, and (b) shows the cell proliferation inhibitory effect in percentage relative to the control group. In this case, the temperature of the tumor cell is maintained in the 40.5° C. range for 1 or 2 hours every day, and it is performed for the total of 3 days.

Referring to (b) of FIG. 8, it can be seen that compared to simply applying electric fields, the application of electric fields with the increasing temperature of the tumor above the body temperature shows about 15% improvement in cell proliferation inhibitory effect.

FIG. 9 is a diagram showing the enhanced cell proliferation inhibitory effect by applying electric fields of 150 kHz after maintaining the temperature of the tumor cell in the range of 39° C. to 42° C. for a predetermined time.

Specifically, FIG. 9 shows the cell proliferation inhibitory effect in percentage relative to the control group by comparing the cell viability through cell counting between the control group and a group (TTF) in which only electric fields having the intensity of ~1 V/cm and the frequency of 150 kHz are applied to malignant glioma cell line (U373) for 3 days, a group (42° C., 40.5° C., 39° C.) in which only heat is applied to maintain the temperature of the tumor cell in the range of 39° C. to 42° C. for 1 hour, and a group (42° C., 40.5° C., 39° C.+TTF) in which electric fields are applied for 3 days after maintaining the temperature of the tumor cell in the range of 39° C. to 42° C. for 1 hour. In other words, with the temperature range, only the viability of cancer cells are affected, whereas that of normal cells does not substantially.

In this aspect, the temperature control according to the present invention leads to heating therapy against cancer cells without affecting normal cell and tissue.

Referring to (b) of FIG. 9, it can be seen that compared to simply applying electric fields, the application of electric fields after increasing the temperature of the tumor above the room temperature and maintaining the temperature for the predetermined time shows about 5-14% improvement in cell proliferation inhibitory effect.

Putting the results of FIGS. 8 and 9 together, it can be seen that when applying electric fields at the same time with maintaining the increased temperature after the increasing the temperature of the tumor above the body temperature, it is possible to inhibit the cell proliferation more effectively.

Additionally, it can be seen that when applying electric fields after increasing the temperature of the tumor cell and maintaining the temperature for the predetermined time, it is possible to inhibit the cell proliferation by the electric fields more effectively. In other words, it can be seen that in the tumor treatment using electric fields, treatment with the increasing temperature of the tumor at the predetermined level for the predetermined time may further improve the treatment effect. In this embodiment, the temperature rise may result in the heating therapy along with the TTF.

Therefore, the system applying electric field to increase temperature to such high level as affecting the viability of cancer cell can be referred to as "heating device" in the present invention. Also, because the heating device uses electric field, conventional electric field therapy device designed to apply electric field and heating device can be integrated into one system where electric field generates. Otherwise, the electric field therapy device and heating device may use separate electric field generating systems.

As described below with reference to FIG. 10 based on the above results, a combined treatment system which increases the temperature of the tumor using the heating device and performs electric field therapy at the same time with or after maintaining the increased temperature for the predetermined period of time may be considered.

Figure 10:
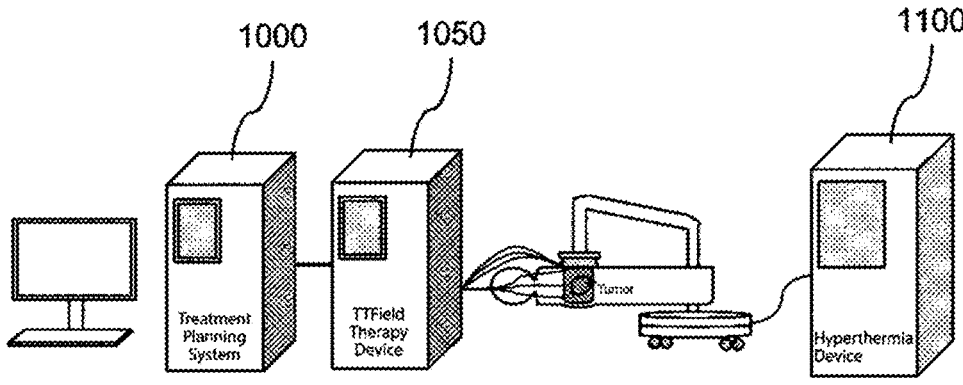
FIG. 10 is a diagram of a system for electric field therapy including a heating device according to an embodiment of the present disclosure.

FIG. 10 is a diagram of a system for electric field therapy including the heating device according to an embodiment of the present disclosure.

Referring to FIG. 10, the system may perform electric field therapy by deriving the optimal electric field treatment plan according to the method for planning tumor-treating electric fields described above with reference to FIG. 7 through the treatment planning system 1000, and applying the result to the electric field treatment device 1050, and maintain the temperature of the region of interest including the tumor at the predetermined level (for example, in the range of 39° C. to 42° C.) for the predetermined time through the heating device 1100 (for example, a high frequency heating device (Hyperthermia Device)).

The combined treatment may be performed not only by performing heat therapy and electric field therapy at the same time, but also by performing the heat therapy to maintain the temperature of the region of interest at the predetermined level for the predetermined time and then performing the electric field therapy.

According to an embodiment of the present disclosure as described above, it is possible to reduce side effects that may occur to normal tissues due to the temperature rise by applying electric fields while monitoring and controlling the temperature of tissues in the body and maximize the electric field treatment effect by performing the electric field therapy with the increasing temperature of the tumor for the predetermined time. In other words, according to an embodiment of the present disclosure, compared to the existing methods for electric field therapy performed without controlling the temperature of tissues in body and tumors, it is possible to provide more reasonable and efficient treatment to patients, and further, overcome the limitations of the existing electric field therapy.

Figure 11:
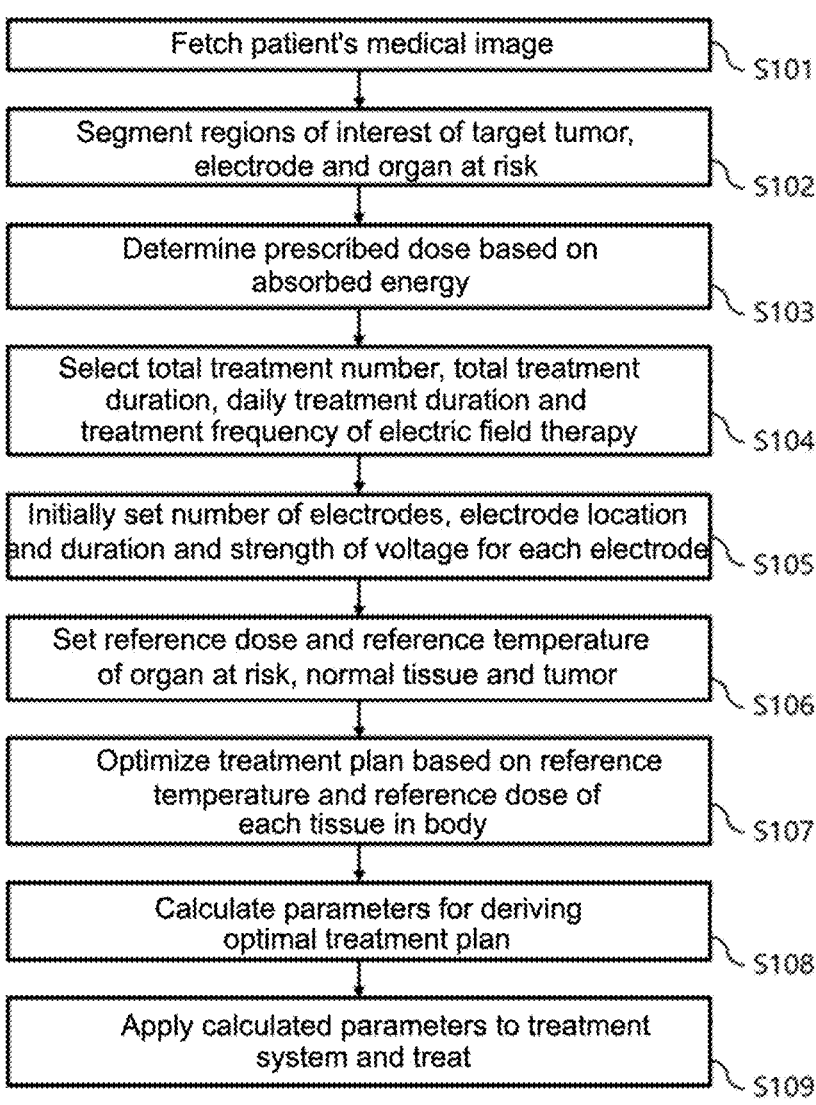
FIG. 11 is a flowchart of a method for electric field therapy based on temperature control and absorbed energy in body according to an embodiment of the present disclosure.

FIG. 11 is a flowchart of a method for electric field therapy based on temperature control and absorbed energy in body according to an embodiment of the present disclosure.

Referring to FIG. 11, first, the patient's medical image (for example, 3-dimensional (3D) medical image data) may be fetched and sent to the treatment planning system (S101) and may be segmented into the regions of interest of the target tumor, electrodes and organs at risk (S102).

Subsequently, the prescribed dose may be determined based on absorbed energy (for example, specific absorbed energy) considering the input tumor type and tumor condition information (S103), and prescription information including the total treatment number, the total treatment duration, the daily treatment duration and the treatment frequency of the electric field therapy may be determined based on the prescribed dose (S104). Here, the frequency may be selected in the frequency band ranging from 10 kHz to 300 kHz.

Subsequently, the number of electrodes, the electrode location and the duration and strength of voltage for each electrode may be initially set considering the location of the tumor and the organs at risk near the tumor (S105), and the reference dose and reference temperature of the organ at risk, the normal tissue and the tumor may be set (S106).

Subsequently, the treatment plan (optimization) process may be performed as described above with reference to FIG. 7 based on the reference temperature and reference dose of each tissue in the body (S107).

Subsequently, the parameters for deriving the optimal treatment plan may be calculated (S108), and the electric field therapy may be performed by applying the calculated parameters to the treatment system (S109).

Figure 12:
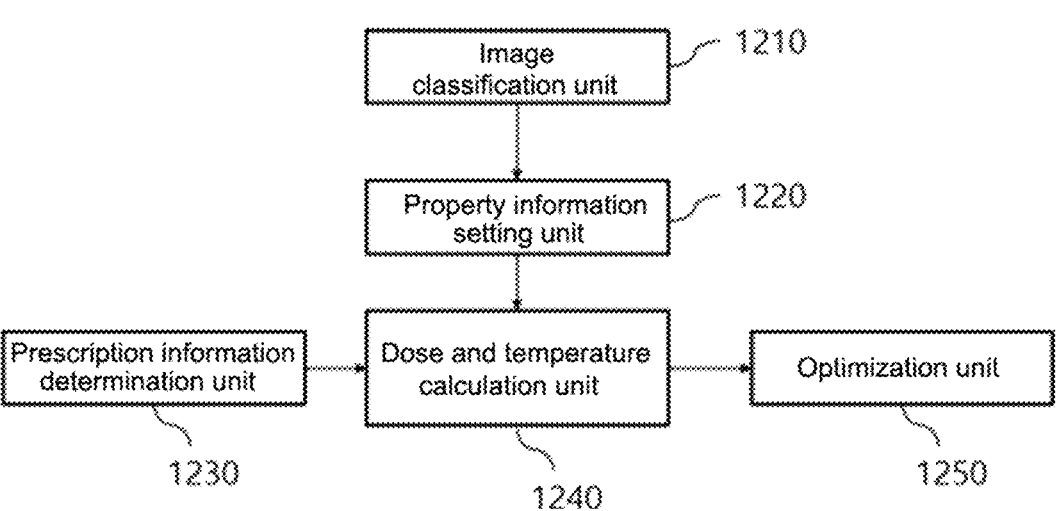
FIG. 12 is an architecture diagram of a system for planning tumor-treating electric fields based on temperature control and absorbed energy in body according to an embodiment of the present disclosure.

FIG. 12 is an architecture diagram of a system for planning tumor-treating electric fields based on temperature control and absorbed energy in body according to an embodiment of the present disclosure.

Referring to FIG. 12, the system 1200 for planning tumor-treating electric fields based on temperature control and absorbed energy in body according to an embodiment of the present disclosure may include an image classification unit 1210, a property information setting unit 1220, a prescription information determination unit 1230, a dose and temperature calculation unit 1240 and an optimization unit 1250.

The image classification unit 1210 may receive the patient's input medical image including organs and a tumor and classify the organs and tumor included in the medical image.

According to an example, the image classification unit 1210 may classify the tumor and each organ from the patient's 3D medical image including the plurality of organs and the tumor, and reconstruct a 3D image for each classified region to identify a positional relationship between the tumor and the plurality of organs.

The property information setting unit 1220 may set property information of each region (for example, the tumor, the organs and other tissues in the human body) classified by the image classification unit 1210.

Here, the property information may include electrical conductivity, thermal conductivity, specific heat and mass density of each tissue in the human body. The electrical conductivity may be set based on magnetic resonance imaging (MRI) or a pre-built electrical conductivity database (DB) for each tissue in the human body. Additionally, the mass density may be set based on computed tomography (CT) or a pre-built mass density DB for each tissue in the human body. Additionally, the thermal conductivity and specific heat may be set based on a pre-built thermal conductivity and specific heat DB for each tissue in the human body.

The prescription information determination unit 1230 may determine the prescribed dose considering the input tumor type and tumor condition information, and determine prescription information including the total treatment number, the total treatment duration, the daily treatment duration and the treatment frequency of electric field therapy based on the prescribed dose. Here, the prescribed dose may be determined by absorbed energy transmitted to the tissues with respect to the preset reference frequency, and when the usage frequency (i.e., treatment frequency) is different from the reference frequency, the prescribed dose may be corrected by applying frequency weights for reflecting the biological effect based on the frequency.

The dose and temperature calculation unit 1240 may initially set the number of electrodes used for the electric field therapy, the electrode location and the duration and strength of voltage for each electrode considering the location and size and the property information of each region (for example, the tumor, the organs and other tissues in the human body) classified by the image classification unit 1210 and calculate the dose distribution and temperature distribution in the body based on the initial settings. Here, the dose distribution in the body may be calculated according to the above Equation 2, and the body temperature distribution may be calculated according to Equation 3.

$$\rho C_p \frac{\partial T}{\partial t} + \nabla \cdot q = \rho_b C_{p,b} W_b (T_b - T) + Q \qquad \text{[Equation 3]}$$

where $\rho$: density of tissues (kg/m$^3$), T: temperature of tissues (K), $\rho_b$: density of blood, $W_b$: perfusion rate of blood (1/s). Q: heat source (W/m$^3$). $C_p$: specific heat of tissue at constant pressure (J/(kg·K)), q: heat flux by conduction in tissues (W/m$^2$), $C_{pb}$: specific heat of blood at constant pressure (J/(kg·K)), and $T_b$: arterial blood temperature (K).

The optimization unit 1250 may perform optimization by changing at least one of the number of electrodes in the electric field cancer treatment device, the electrode location, the duration or strength of voltage for each electrode so that the temperature of the normal tissues and the tumor meets the preset reference temperature, and the prescribed dose is delivered to the tumor to the maximum while minimizing the dose for the normal tissues near the tumor below the preset reference (i.e., the dose for each region meets the preset reference dose).

The present disclosure is not limited by the above-described embodiments and the accompanying drawings. It will be obvious to those skilled in the art that substitution, modifications and changes may be made to the elements according to the present disclosure without departing from the technical spirit of the present disclosure.

The invention claimed is:

1. A system for planning tumor-treating electric fields based on temperature control and absorbed energy in body, comprising:

a treatment planning system including at least one processor configured to:

initially set a number of electrodes, an electrode location, a duration and strength of voltage for each electrode;

calculate absorbed dose and temperature distribution in the body based on the initial settings;

evaluate the calculated absorbed dose and temperature distribution in the body to determine if they meet a preset reference;

change at least one of the number of electrodes, the electrode location, the duration or strength of voltage for each electrode when the preset reference is not met;

derive an optimal electric field treatment plan by performing an optimization process including repeating the calculation step, the evaluation and the changing until the calculated absorbed dose and temperature distribution in the body meet the preset reference; and calculate the absorbed dose distribution as a distribution of specific absorbed energy for each tissue, the specific absorbed energy being calculated as (power loss density×duration of applied electric fields)÷mass density.

2. The system of claim 1, wherein the processor is configured to initially set the number of electrodes, the electrode location, the duration and strength of voltage for each electrode based on pre-input patient information.

3. The system of claim 1, wherein the processor is further configured to:

segment a region of interest including a tumor and an organ in a patient's medical image;

determine a prescribed dose based on absorbed energy, the prescribed dose being determined in consideration of input tumor type and tumor condition information; and determine prescription information including a total treatment number, a total treatment duration, a daily treatment duration and a treatment frequency for electric field therapy;

wherein the processor initially sets the number of electrodes, the electrode location, the duration and strength of voltage for each electrode in consideration of the tumor and organ.

4. The system of claim 1, wherein the processor utilizes property information of human body when evaluating the the calculated absorbed dose and temperature distribution.

5. The system of claim 4, wherein property information includes electrical conductivity, thermal conductivity, specific heat and mass density of each tissue in the human body.

6. The system of claim 5, wherein the electrical conductivity is set based on magnetic resonance imaging (MRI) or a pre-built electrical conductivity database (DB) for each tissue in the human body.

7. The system of claim 5, wherein the mass density is set based on computed tomography (CT) or a pre-built mass density DB for each tissue in the human body.

8. The system of claim 5, wherein the thermal conductivity and specific heat are set based on a pre-built thermal conductivity and specific heat DB for each tissue in the human body.

9. A system for performing electric field therapy, comprising the system for planning tumor-treating electric fields based on temperature control and absorbed energy in the body according to claim 1;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

10. The system of claim 9, wherein the preset temperature range affects only cancer cells without affecting normal cells substantially.

11. A system for performing electric field therapy, comprising the system for planning tumor-treating electric fields based on temperature control and absorbed energy in the body according to claim 2;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

12. A system for performing electric field therapy, comprising the system for planning tumor-treating electric fields based on temperature control and absorbed energy in the body according to claim 3;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to the plan set by the treatment planning system at the same time with or after the heat therapy.

13. A system for performing electric field therapy, comprising the system for planning tumor-treating electric fields based on temperature control and absorbed energy in the body according to claim 4;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

14. The system of claim 13, wherein the preset temperature range affects only cancer cells without affecting normal cells substantially.

15. A system for performing electric field therapy, comprising the system for planning tumor-treating electric fields based on temperature control and absorbed energy in the body according to claim 5;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

16. The system of claim 15, wherein the preset temperature range affects only cancer cells without affecting normal cells substantially.

17. A system for performing electric field therapy, comprising the system for planning tumor-treating electric fields based on temperature control and absorbed energy in the body according to claim 6;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

18. A system for performing electric field therapy, comprising the system for planning tumor-treating electric fields based on temperature control and absorbed energy in the body according to claim 7;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

19. A system for performing electric field therapy, comprising the system for planning tumor-treating electric fields based on temperature control and absorbed energy in the body according to claim 8;

an electric field therapy device performing electric field therapy in compliance with a plan set by the system for planning tumor-treating electric fields based on temperature control and absorbed energy in body;

and a heating device;

wherein the heating device performs heat therapy by maintaining the temperature of a region of interest including a tumor in a preset temperature range for a preset time, and the electric field therapy device performs electric field therapy according to a plan set by the treatment planning system at the same time with or after the heat therapy.

20. The system of claim 19, wherein the preset temperature range affects only cancer cells without affecting normal cells substantially.

* * * * *